United States Patent [19]
Berndt et al.

[11] Patent Number: 5,196,709
[45] Date of Patent: Mar. 23, 1993

[54] FLUOROMETRY METHOD AND APPARATUS USING A SEMICONDUCTOR LASER DIODE AS A LIGHT SOURCE

[75] Inventors: Klaus W. Berndt; Ignacy Gryczynski, both of Baltimore; Joseph R. Lakowicz, Columbia, all of Md.

[73] Assignee: University of Maryland Systems, Baltimore, Md.

[21] Appl. No.: 695,074

[22] Filed: May 3, 1991

[51] Int. Cl.[5] .............................................. G01N 21/64
[52] U.S. Cl. .............................. 250/458.1; 250/459.1; 356/318
[58] Field of Search .................... 250/458.1, 459.1; 356/318, 417; 436/172

[56] References Cited

U.S. PATENT DOCUMENTS 4,895,156  1/1990  Schulze ........................... 250/458.1

FOREIGN PATENT DOCUMENTS 2224352  5/1990  United Kingdom ................ 356/318

OTHER PUBLICATIONS

Reid et al "Measurement of the Transition Strength of . . . Sequence Band in $CO_2$ . . . " App. Phys. 17, No. 4, Dec. 1978, pp. 349-353.

Vo-Dinh et al "Phase resolved . . . Fluoroimmunosensor" App. Spect. vol. 44, No. 1, Jan. 1990, p. 128.

*Primary Examiner*—Constantine Hannaher
*Assistant Examiner*—Richard Hanig
*Attorney, Agent, or Firm*—Sughrue, Mion, Zinn, Macpeak & Seas

[57] ABSTRACT

A method and apparatus for detecting the change in phase angle and/or modulation of emitted fluorescence of a fluorophore excited by modulated light from a laser diode. The light is both monochromatic and coherent, and can contain harmonic frequency components. The laser diode can be used in frequency-domain or phase-modulation measurements of fluorescence, using either phase or modulation techniques. The present invention is an improvement of the prior use of a frequency-doubled, cavity-dumped, dye laser in fluorometers. The invention provides an inexpensive light excitation source that is small in size, easily manageable, allows for short measurement times, and has lower power requirements.

16 Claims, 3 Drawing Sheets

FLUOROMETRY METHOD AND APPARATUS USING A SEMICONDUCTOR LASER DIODE AS A LIGHT SOURCE

FIELD OF THE INVENTION

The invention relates generally to the field of fluorometry and, more particularly, to a method and apparatus for using a laser diode as a source of excitation light for a fluorophore and detecting changes in phase angle and/or modulation of the emitted fluorescence as parameters which correspond to fluorescence lifetimes.

BACKGROUND OF THE INVENTION

Fluorescence measurements are conventionally used in flow cytometry, fluorescence microscopy, and fluorescence spectroscopy. With few exceptions, such measurements are of the steady state emission signal, as intensity changes or wavelength shifts. Such measurements are often aimed towards determination of the concentration of fluorophore or analytes. The precise and accurate measurement of known intensity- or wavelength shift-based sensing has suffered from problems such as delayed results, the need for expensive, sophisticated and time consuming procedures that are limited, e.g., by high background noise, low signal-to-noise ratios, turbidity, optical losses, photobleaching and fluorophore washout; the need for alternative ranges of wavelength sensing; the need for continuous or immediate results; the need for containment of hazardous or potentially hazardous samples; the need for remote sensing; and/or the need for continuous or repetitive sampling.

These problems have the potential to be minimized or eliminated by the use of a measuring system based on fluorescence lifetime (or decay) measurements which are insensitive to changing instrument conditions and which are independent of the intensity fluctuations of fluorescence radiation. Fluorescence lifetime measurements can be performed in the time-domain by using the known time-correlated single photon counting (TCPSC) technique, or in the frequency-domain by measuring the phase shift and modulation of the fluorescence emission with respect to a amplitude-modulated sinusoidal excitation as a function of frequency.

In a TCPSC time-domain lifetime measurement system, the time dependent probability of fluorescence photon emission after pulsed excitation is measured by statistical counting of the arrival time of individual photons. However, the experimental data produced gives the fluorescence decay in a form that is convoluted with the instrument response function, and the use of time domain lifetime measurements are presently more expensive, time consuming and complex than frequency-domain measurements. See, e.g., "Pulsed Semiconductor Laser Fluorometry for Lifetime Measurements", Analytical Chemistry, vol. 57, no. 4, April 1985, pp. 947-949.

In a conventional frequency-domain lifetime measurement system, a sample is excited with light from an intensity-modulated light source. Lifetime measurements are made by measuring the frequency response of the sample, i.e., the frequency-dependent phase angle and modulation of the fluorescence emitted from the sample. The emitted fluorescence is modulated at the same frequency as the excitation light but is shifted in phase and demodulated with respect to the excitation light.

For the case of pure sinusoidally modulated excitation and a single exponential decay, the phase shift $\phi$ and modulation ratio M of the fluorescence versus excitation are related to the excited state lifetime $\tau$ of the fluorophore and the modulation frequency $\omega$ by the following relations:

$$\tan\phi = \omega\tau$$

$$M = M_f/M_r = (1+\omega^2\tau^2)^{-\frac{1}{2}}$$

where $M_r$ and $M_f$ are respectively the excitation and fluorescence modulation amplitudes referenced to their respective DC levels. See, e.g., Lakowicz PRINCIPLES OF FLUORESCENCE SPECTROSCOPY Plenum Press, New York (1983). Also see, "AN AUTOMATED PHASE FLUOROMETER WITH HIGH PRECISION RESOLUTION FOR MULTI-EXPONENTIAL FLUORESCENCE DECAYS", by Clays, Engelborghs and Persons; REVIEW OF SCIENTIFIC INSTRUMENTS, 1988.

For a multi-exponential decay (wherein decays are present that are due to more than one fluorophore or analyte with differing lifetimes) the relations are $$\tan\phi = S/G \text{ and } M^2 = S^2 + G^2$$

where $S = \Sigma_i f_i \cos\phi_i \sin\phi_i$, and $G = \Sigma_i f_i \cos^2\phi_i$, $f_i$ is the fraction of the total intensity from the ith component, and $\phi_i$ is the phase shift.

For a non-exponential decay, S and G should be calculated as the real and imaginary part of the Fourier transform of the response function I(t):

$$S(\omega) = \int_0^\infty I(t) \sin \omega t \, dt$$

$$G(\omega) = \int_0^\infty I(t) \cos \omega t \, dt.$$

where I(t) is the time domain response function to a delta excitation function.

Suppose the excitation source produces a train of pulses, equally spaced in time, with constant repetition frequency $f_0 = 1/T$, constant shape (e.g., Gaussian), constant amplitude and width $2\Delta$, then the timing function of such a light source is given by $$I(t) = \frac{1}{\Delta\sqrt{2\Pi}} \Sigma_n \exp(-(t-nT)^2/4\Delta^2)$$

$$n = 0, 1, 2, \ldots,$$

and the harmonic content in the power spectrum is given by its Fourier transform $$G(f) = \delta(f - nf_0) \exp(-\frac{1}{2}(\Delta \cdot f)^2) n = 1, 2, 3, \ldots$$

where $\delta$ is defined as the Dirac delta function, e.g., as described by K. Berndt, H. Durr and D. Kalme in Optics Communications, 1982, vol. 42, pp. 419-422.

If the pulse is short, the harmonic content in the power spectrum is high and energy is available over a wide range of frequencies. When excited with such a light source, the fluorescence of the sample will be modulated at all the higher harmonics of the pulse repetition frequency at the same time. Monitoring the phase shift at successive higher harmonics of the fundamental excitation frequency reveals information on the fluorescence decay. By measuring the phase shift at many harmonics in the power spectrum, the fluorescence lifetime resolution is increased, a feature which is particularly important for multi-exponential decays.

For example, the above described excitation source may be a synchronously pumped, cavity-dumped dye laser made by Spectra Physics (no. 375B), with Rhodamine 6 G (R6G) or 4-dicyanomethylene-2-methyl-6-p-dimethylaminostyryl-4H-pyran (DCM) as the dye, pumped by the 514.5 nm green line of a mode locked Argon-ion laser (Spectra Physics 2030). Dye lasers of this type provide wavelengths ranging from 570 nm to 720 nm. Cavity dumping provides for more narrowly spaced harmonics at multiple frequencies, and frequency doubling of the laser output achieves excitation wavelengths in the ultraviolet (UV) frequency range, e.g. 285-340 nm. This UV output, used as an excitation light source, is useful for many fluorescence studies. The dye laser is equipped with a cavity dumper (Spectra Physics 344S) to reduce the pulse repetition frequency from the mode locked dye laser.

The pulsed laser source is thus advantageous in that the high peak power results in rather easy and efficient frequency doubling. The light output is intrinsically modulated over a wider range of frequencies, beyond that obtainable with any commercially available broadband modulator or other additional optical device that would otherwise be required. Using the harmonic content of the pulsed output of the dye laser as an excitation source considerably improves the accuracy and resolution of phase measurements. In this manner, phase shift data can be read out within a relatively short measurement time. All the harmonics within the bandwidth of the system are of comparable amplitude because of the very high bandwidth of the excitation function.

However, the above described laser system is extremely expensive, requires considerable space and power, and is difficult to align and maintain. Thus, there is a need for a fluorescence lifetime measuring apparatus and method which provide improved accuracy, shorter measurement times and lower power requirements, without the high cost and maintenance problems of the prior art systems.

SUMMARY OF THE INVENTION

It is therefore an object of the present invention to overcome the above problems relating to fluorescence sensing by providing an improved apparatus and methods in which a laser diode is used as an excitation light source.

It is another object of the present invention to provide apparatus and methods that utilize a laser diode for frequency-domain or phase modulation measurements of fluorescence, using either phase or modulation measurement techniques.

It is another object of the present invention to provide apparatus and methods using as an excitation light source, such as a laser diode, which can be modulated over a wide range of frequencies, or a pulsed light source, for measuring a fluorescence lifetime, phase angle or modulation of an emission of an excited fluorophore as a determination of a condition, such as the presence or concentration of an analyte, or other environmental change of the fluorophore.

Another object of the present invention is to provide methods and apparatus which use a laser diode for analyte sensing of samples comprising compounds, mixtures, surfaces, solutions, emulsions, suspensions, mixtures, cell cultures, fermentation cultures, cells, tissues, secretions and/or derivatives or extracts thereof, and which are independent and/or insensitive to photobleaching, probe washout and/or optical losses. It should be noted that tissues have minimal absorbance at the fundamental wavelengths of laser diodes (e.g., 600-1000 nm). This fact, together with the independence of lifetimes from scattering, results in opportunities for lifetime sensing using the modulated output of the laser diodes.

Another object of the present invention is to provide methods and apparatus using a laser diode light sources for analyte sensors which are based on measurement of fluorescence lifetimes and which would thereby provide continuous monitoring of an analyte or parameter dependent on the presence or concentration of said analyte, in a sample as defined herein, such as pH, $pCO_2$, $H^+$, $OH^-$, $CO_2$, $H_2CO_3$, $HCO_3^-$, $K^+$, $Ca^{++}$, ions, or other samples containing these analytes or parameters.

Another object of the present invention is to provide methods and apparatus using a laser diode as a light source for analyte sensing measurements utilizing fluorescence lifetimes which monitor analyte conditions in cell culture and/or fermentation cultures.

According to one aspect of the present invention, an apparatus is provided for detecting a change in phase angle and/or modulation, corresponding to a change in lifetime, of a fluorescence emission of at least one fluorophore comprising:

semiconductor laser diode means which outputs modulated light when driven by a first electrical signal, said light being substantially monochromatic and coherent;

first electrical signal generator means, coupled to said semiconductor laser diode means, for generating said first electrical signal to cause said semiconductor laser diode means to output said modulated light having a wavelength which excites said at least one fluorophore to emit fluorescence; and second electrical signal generator means, coupled to at least one of said first electrical signal generator means and a fourth electrical signal corresponding to the output of said laser diode means, said second electrical signal generator means for generating a second electrical signal that is phase locked to said output of said laser diode means;

photodetector means for sensing said emitted fluorescence, said photodetector means coupled to at least said second electrical signal generator means to provide a third electrical signal which is compared to said second signal to generate a difference representative of a change in phase angle and/or modulation of said emitted fluorescence of said at least one fluorophore, wherein said change corresponds to a change in fluorescence lifetime.

In another embodiment, the laser diode means further comprises a photodiode that generates the fourth electrical signal corresponding to the output of the laser diode and (b) the second electrical signal is compared to the third electrical signal to provide the change in phase angle and/or modulation of the emitted fluorescence of the at least one fluorophore, wherein said change corresponds to a fluorescence lifetime.

In another embodiment, the laser diode means outputs the modulated light with a plurality of frequency components that are harmonics of the first electrical signal. In a preferred embodiment, the wavelength of the modulated light is in the range of about 250-1600 nm and said wavelength is selected from (i) a fundamental wavelength of said output of said laser diode means; and (ii) a resultant wavelength, after frequency doubling, of a fundamental wavelength of said output of said laser diode means.

In another embodiment, wherein the laser diode means is intrinsically or extrinsically modulated in the frequency range of about 10 Khz to 20 GHz.

In another embodiment, the photodetector means comprises a means for measuring relative modulation of said third and said second electrical signals as an indication of said change in phase angle and/or modulation of said emitted fluorescence of said at least one fluorophore. In a preferred embodiment, the photodetector means comprises a photomultiplier tube for detecting the emitted fluorescence.

In another embodiment, the detecting is done in the frequency-domain.

In another aspect of the present invention, a method is provided for detecting changes in phase angle and/or modulation, corresponding to changes in lifetime, of emitted fluorescence of at least one fluorophore in a sample, comprising:

driving a semiconductor laser diode means with a first electrical signal to cause said semiconductor laser diode means to output modulated light having a wavelength capable of exciting said at least one fluorophore to emit fluorescence, wherein said modulated light is monochromatic and coherent;

exciting said at least one fluorophore with said modulated light to produce a fluorescence emission;

generating a second electrical signal, coupled to said first electrical signal or to a fourth electrical signal corresponding to the output of said laser diode means, said second electrical signal being phase locked to said output of said laser diode means;

sensing said fluorescence emission to provide a third electrical signal corresponding to said fluorescence emission; and comparing said second electrical signal with said third electrical signal to generate a difference representative of said change in phase angle and/or modulation, corresponding to a change in lifetime, of said emitted fluorescence of said at least one fluorophore.

In one embodiment, the laser diode outputs modulated light with a plurality of frequency components that are harmonics of the electrical signal.

In another embodiment, the wavelength is in the range of about 250-1600 nm, and the wavelength is selected from (i) a fundamental wavelength of said output of said laser diode means; and (ii) a resultant wavelength, after frequency doubling, of a fundamental wavelength of said output of said laser diode means.

In another embodiment, the comparing step comprises measuring a phase difference between said corresponding third electrical signal of said emitted fluorescence and the second electrical signal.

In another embodiment, the change corresponds to the presence or concentration an analyte in a sample, wherein said sample is a compound, a mixture, a surface, a solution, an emulsion, a suspension, a mixture, a cell culture, a fermentation culture, a cell, a tissue, a secretion or a derivative or extract thereof. In another embodiment, the analyte comprises a salt, a derivative, a polymer, a dissociation product, or aggregate of said analyte. In a preferred embodiment, the analyte is selected from $H^+$, $OH^-$, $CO_2$, $H_2CO_3$, $HCO_3$, $Ca^{++}$ or $K^+$.

In another embodiment, the method comprises a frequency-domain fluorescence lifetime measurement or a phase-sensitive fluorescence intensity measurement.

In another embodiment, the modulated light is intrinsically modulated or extrinsically modulated.

The apparatus according to the invention provides a semiconductor device, particularly a laser diode, as an inexpensive excitation light source for fluorometric sensors or fluorometers. A modulated electrical input to the laser diode causes a very large number of photons to be emitted in the form of a modulated light output having a large harmonic content.

Accordingly, the present invention provides a fluorescence sensing system with an inexpensive light source, that is small in size and power requirement, and easy to align and maintain.

Further advantages and features of the invention will become apparent from the following description, claims, and drawings, which are directed to preferred embodiments of the invention.

DESCRIPTION OF PREFERRED
EMBODIMENTS OF THE INVENTION

Measurements of fluorescence lifetimes are being used increasingly in chemical, biochemical, and biophysical research. Fluorescence lifetime data may be obtained either by direct measurements in the time-domain, as described above, or by the alternative technique of frequency-domain fluorometry. As described above, the latter requires measurement of change in phase angle or modulation of a fluorescence emission, relative to the intensity-modulated exciting light, which relative change be measured over a wide range or modulating frequencies. The intensity-modulated exciting light can be obtained by modulating the output of a continuous-wave (CW) laser, using electro- or acoustic-optic devices for extrinsic modulation. In recent years, the preferred light source for frequency-domain fluorometry has become a synchronously pumped and cavity dumped dye laser. Owing to their high peak power, these lasers allow efficient frequency doubling over extended wavelength ranges, yielding tunable short-wavelength excitation radiation. Importantly, the output of the pulse train is intrinsically modulated at all related harmonics of the pulse repetition rate, up to hundreds of megahertz (Mhz) or even to several gigahertz (Ghz). As noted above, however, these laser systems are very expensive, require considerable lab space, and are difficult to align and maintain.

According to the present invention, a modulated semiconductor laser diode is provided as a superior alternative excitation-light source, which can be intrinsically modulated over a wide range of frequencies. Additionally, the laser diode can be operated in a pulsed mode, producing harmonics of the pulse repetitive rate. Additionally, the output can be frequency doubled to produce a excitation-light having an effective wavelength that is half of the fundamental wavelength.

Additionally, methods and apparatus of the present invention, using a laser diode light source, are provided that comprise steps or means for illuminating a sample comprising a fluorophore and an analyte, wherein the fluorophore is excited by the laser diode light source such that the emission of the fluorophore has a changed phase angle and/or modulation, corresponding to a change in lifetime, responsive to the environment or presence of at least one analyte. According to apparatus and methods of the present invention, the measuring of a change in at least one of phase angle and modulation of the emitted fluorescence of at least one fluorophore can be used to sense the analyte, wherein the change in lifetime, phase angle or modulation is responsive to the presence or concentration of the analyte.

In the context of the present invention, the term "sample" refers to compounds, mixtures, surfaces, solutions, emulsions, suspensions, mixtures, cell cultures, fermentation cultures, cells, tissues, secretions and/or derivatives or extracts thereof. Samples, as defined above, which can be used in methods or apparatus of the present invention for detecting analytes based on sensing fluorescence emissions and comparing the correponding electrical signal to a reference signal corresponding to the phase locked output of the exciting light. Such comparison of changes in the resulting phase angle and/or modulation, corresponding to changes in the lifetime of at least one fluorophore in the sample, also include samples that can be clear or turbid. Such samples to be measured according to the present invention require only that the fluorophore used be contacted with the sample such that the analyte to be sensed influences the lifetime of the fluorophore such that the phase angle and/or modulation, corresponding to the lifetime, of the emitted fluorescence of the excited fluorophore varies with the presence or amount of the analyte.

Such samples can also include, e.g., animal tissues, such as blood, lymph, cerebrospinal fluid (CNS), bone marrow, gastrointestinal contents, and portions, cells or internal and external secretions of skin, heart, lung and respiratory system, liver, spleen, kidney, pancreas, gall bladder, gastrointestinal tract, smooth, skeletal or cardiac muscle, circulatory system, reproductive organs, auditory system, the autonomic and central nervous system, and extracts or cell cultures thereof. Such samples can be measured using methods of the present invention in vitro, in vivo and in situ. It should be noted that organic tissues have minimal absorbance at the fundamental wavelengths of laser diodes (e.g., at 600–1000 nm). This fact together with the characteristic independence of lifetime from light scattering, results in opportunities for lifetime sensing using the modulated output of laser diodes, which are not possible using conventional intensity or wavelength shift methods.

Such samples can also include environmental samples such as earth, air or water samples, as well as industrial or commercial samples such as compounds, mixtures, surfaces, aqueous chemical solutions, emulsions, suspensions or mixtures.

Additionally, samples that can be used in methods of the present invention include cell culture and fermentation media used for growth of prokaryotic or eukaryotic cells and/or tissues, such as bacteria, yeast, mammalian cells, plant cells and insect cells.

The term "analyte" in the context of the present invention refers to elements, ions, compounds, or salts, dissociation products, polymers, aggregates or derivatives thereof. Examples of analytes that can be used in methods of the present invention include, e.g., $H^+$, $OH^-$, $CO_2$, $H_2CO_3^-$, $HCO_3^-$, $K^+$, $Ca^{++}$, ions or other compounds containing these ions or compounds, including salts, derivatives, polymers, dissociation products, or aggregates thereof.

Fluorophores suitable for use in methods according to methods of the present invention include fluorophores whose lifetimes vary reproducibly with a condition of the microenvironment, such as the concentration or amount of a particular analyte, as described herein, and which lifetimes are detectable by known fluorescence spectroscopy methods. It has been discovered that fluorophores previously only known to vary reproducibly in intensity or wavelength shifts in reponse to the presence or concentration of an analyte.

Examples of fluorophores that can be used in methods and apparatus of the present invention, now discovered to have lifetimes which change with the presence or concentration of an analyte, include a seminaphthofluorescein, a seminapthorhodafluor, a alkyl substituted or unsubstituted resorufin, a 2',7'-bis-(2-carboxyethyl)-5-(and-6) carboxyfluorescein for $CO_2$ sensing; PBFI for $K^+$ sensing; and QUIN-2 for $Ca^{++}$ sensing (available from Molecular Probes, Inc. Junction City, Oreg.).

Accordingly, fluorophores suitable for use in methods and apparatus of the present invention include fluorophores that have fluorescence lifetimes which vary continuously over a suitable range of analyte concentrations or amounts, and are excitable with a suitable chromatic light, such as a laser diode light at a corresponding wavelength or which can be frequency doubled to produce such a light. Thus, the present invention provides for apparatus and methods for condition sensing of a sample, such as analyte sensing, using a detection of a change in phase angle and/or modulation, corresponding to a change in lifetime, of an fluorescence emission of a fluorophore and includes all fluorophores meeting the above criteria. These criteria are set forth in the copending application Ser. No. 07/694,282 by Joseph R. Lakowicz and Henry Szmacinski entitled METHOD FOR OPTICALLY MEASURING CHEMICAL ANALYTES, filed May 3, 1991, the entire contents of which are herein incorporated by reference. Therefore, fluorophores suitable for use in methods and apparatus of the present invention are not limited to the types and examples described herein.

Furthermore, fluorophores (suitable for use in methods of the present invention for detection of a change in phase angle and/or modulation, corresponding to a change in lifetime, of an emission fluorescence of a fluorophore influenced by a condition, such as the presence or concentration of an analyte), are commercially available, and are now discovered by the present inventors to correspond to those fluorophores which can be used for analyte (as those analytes disclosed herein) detection or quantitation using intensity or wavelength shift fluorometry, e.g., from Molecular Probes, Inc., Junction City, Oreg.

Figure 1:
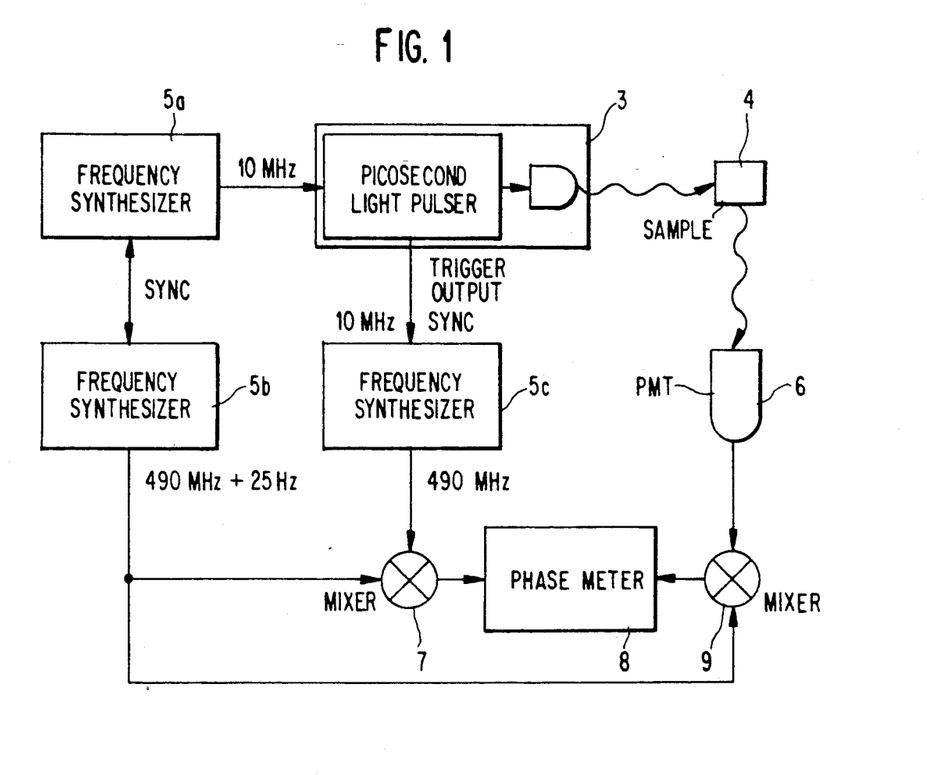
FIG. 1 is a block diagram of a laser diode, frequency-domain fluorometer according to the present invention.

An example of a laser-diode frequency-domain fluorometer according to the present invention is shown in FIG. 1. A laser diode 3, consisting of a laser diode head with a thermoelectric controller (not shown), emits a series of output light pulses with a maximum repetition frequency in the Khz to Mhz range, preferably in the range of 5 to 10 Mhz. A constant peak power of at least about 0.1 mW, and more preferably at least about 0.5 mW, is preferred. Pulse durations can be used in the range of 5 to 50 ps. The pulsed light source has an average power of 220 nW at the 10 MHz repetition rate. Laser diodes can be intrinsically modulated to several GHz (see for instance N. Bar-Chaim, K. Y. Lau, I. Ury, and A. Yaric *Appl. Phys. Lett.* 43:261-262 (1983) and Ortel Corporation Application Manual "High Speed Laser Diodes), and this output can be used for phase-modulation fluorometry.

Thus, an example of a laser light source according to the present invention operates as an intensity-modulated light source at a pulse repetition frequency, and has all the harmonics of that frequency. Owing to the short pulse duration of about 40 ps, efficient intensity-modulation is available up to 11 GHz. In an alternative embodiment, the laser diode can be intrinsically modulated at the desired frequency. A fluorophore-containing sample 4 is positioned close to the laser diode head in order to capture as much excitation light as possible. The diode laser 3 generates an electrical trigger output via a first frequency synthesizer 5a, which is synchronized with a second frequency synthesizer 5b. Any periodic electrical trigger with a high enough frequency would be adequate, as long as the mixers 7 and 9 are driven coherently with the trigger signal. The second frequency synthesizer 5b is used to coherently drive the mixers 7 and 9. Frequency synthesizers 5a and 5b thus are phase-locked to the diode laser, preferably within one Hz per $10^8$ Hz, and generate the local oscillator signal (LO) for the mixers 7 and 9.

A microchannel plate (MCP) photo-multiplier (PMT) 6 can be used to measure scattered radiation from the diode laser 3, as well as measure fluorescence light from the sample 4. A PMT 6 can be an externally cross-correlated micro-channel plate PMT. Alternatively, one can use an avalanche photodiode or other simple detectors with the same or similar external cross-correlation circuits. Also, one can use a standard dynode PMT which is internally cross-correlated by gain modulation at a dynode within the PMT. Such techniques are well known in the art. The technique of cross-correlation is well known for its use in phase-modulation or frequency-domain fluorometers as a means to increase the signal-to-noise ratio and to reject unwanted harmonics.

Photosensitive devices suitable for use in methods and apparatus of the present invention include, e.g., photomultiplier tubes (PMTs); microchannel plate PMTs; photodiodes including silicon, germanium, and gallium arsenide; avalanche photodiodes; photoresistors; photoconductive cells; photogenerative devices; photoelectric cells; and charge-coupled devices. Such photosensitive devices, used as photodetectors in the present invention, can be used singly or in arrays.

In the present apparatus the output signal from the PMT 6 is down-mixed to 25 Hz in the signal mixer 9, and input to a phase meter 8. The down-mixed signal can vary over a wide range, with values from 10 Hz to 15 MHz having been reported in the literature. Preferred values are from 10 Hz to 100 kHz. The phase meter 8 also receives an input signal from reference mixer 7 for comparison with the input signal from signal mixer 9. A direct current (DC) signal channel (not shown) also can connect the PMT 6 with the phase meter 8. The AC signal and the DC signal are processed within the phase meter 8 to obtain the modulation information, which is the ratio of the AC/DC components of the modulated emission. The reference mixer 7 and the signal mixer 9, in the above-described configuration, allow the PMT 6 output to contain the full harmonic content of the fluorescence signal.

Phase meters suitable for use in methods and apparatus of the present invention include the Stanford Research Systems Model SR530, the EG&G Princeton Applied Research Model 5210, and many other types.

In order to be useful for frequency-domain fluorometry, the pulsed laser diode should provide harmonic content over a wide range of modulation frequencies.

A controller of the laser diode 3 system can also be equipped with an electrical trigger output. The laser diode 3 can be triggered at a 10 MHz frequency-synthesizer clock frequency (FIG. 1). In this case, the laser diode 3 trigger output has a 10 MHz frequency, which can be used to phase-lock the third frequency synthesizer 5c. Any drift of the trigger output signal of the laser diode 3 is transferred to this third frequency synthesizer 5c whose output signal frequency can be set to any harmonic of the laser pulse repetition frequency.

A high-speed PIN photodiode, integrated into the laser head, according to the present invention, can be used to generate a short and drift-free trigger output pulse. To drive the photodiode, scattered or reflective NIR could be used. Alternatively, an optical NIR reference output can be used.

Alternative apparatus suitable for use in the present invention, includes components available from C-STAR OPTICS of Seattle, Wash., and from MELLES GRIOT of Irvine, Calif. For example, from C-STAR, a model CL-20078 diode laser can be used with an Sharp LT-023 signal generator, an LD-2000 driver, as mounted in an AC-9500 thermoelectric temperature head with an AC-9603 modulation head. From MELLES-GRIOT, a diode driver model 06 DLD 003 can be used with a 06 DLH 001 high frequency cable, a 06 DTC 003 thermoelectric cooler head and a 06 OLDL 201 780 nm diode head.

Figure 3:
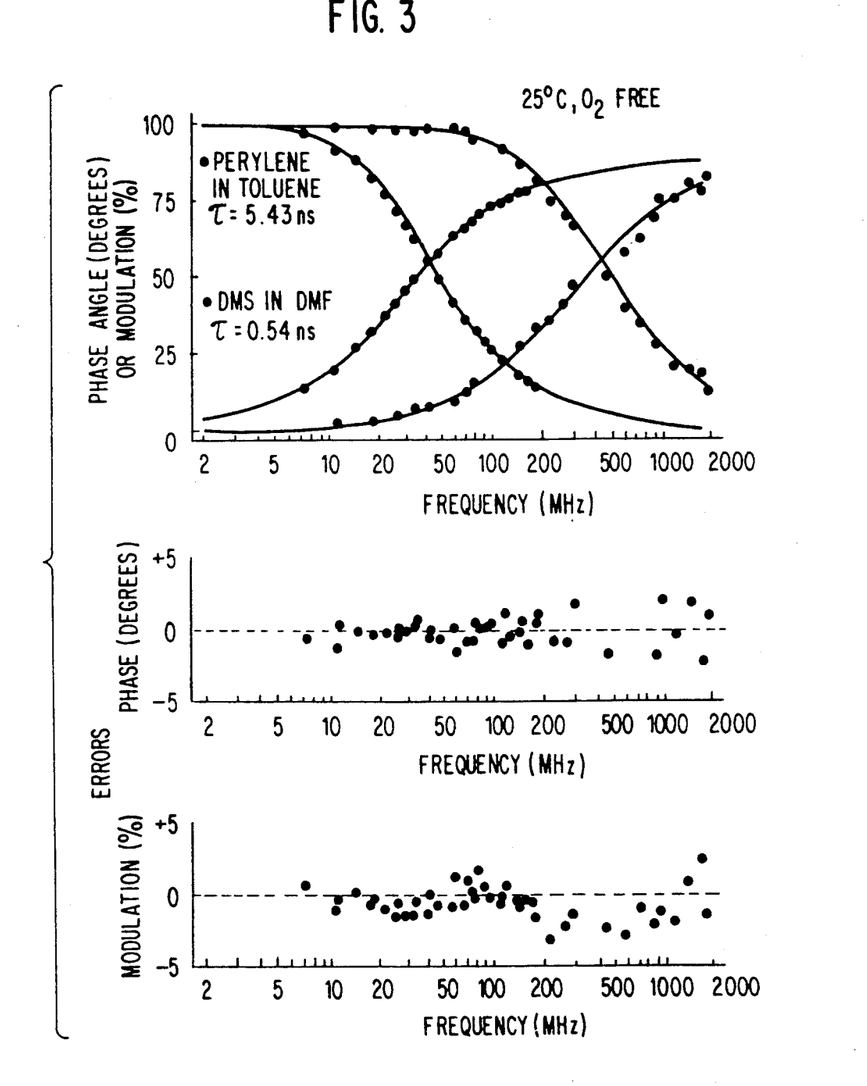
FIGS. 3 and 4 are graphs of phase and modulation data for individual fluorophores or mixtures of fluorophores, as measured by a fluorometer according to the present invention.

Apparatus according to the present invention can be used with fluorophores with lifetimes ranging from about 50 ps to 100 ns. Fluorophores used according to the present invention are preferably chromatographically pure and can be placed in spectroscopic grade toluene and dimethylformamide solvents. The solutions can be purged by nitrogen before the measurements. Emissions can be observed through a band-pass filter which absorbs the diode laser emission and/or scattered light below a desired wavelength, depending on the fluorophore used. For example, frequency responses for perylene in toluene and 4-dimethylamino-4'methoxystilbene (DMS) in dimethylformamide are shown in FIG. 3.

For this fluorophore analysis, the intensity decay is assumed to be described by a sum of exponential components $$I(t) = \Sigma a_i e^{-t/Y_i},$$

where $a_i$ are the preexponential factors, $Y_i$ the decay times, and $\Sigma a_i = 1$. The assumed parameter values ($a_i$ and $Y_i$) are used to calculate the expected phase ($\phi_{wc}$) and modulation ($m_{wc}$) at each modulation frequency $\omega$. The $a_i$ and $Y_i$ values are selected to yield the best fit to the measured data ($\phi_w$ and $m_w$), as judged by the goodness-of-fit parameter $\chi_R^2$, $$\chi_R^2 = \frac{1}{\nu} \sum_i \left( \frac{\phi_w - \phi_{wc}}{\delta\phi} \right)^2 + \frac{1}{\nu} \sum_i \left( \frac{m_w - m_{wc}}{\delta m} \right)^2.$$

In this expression, $\nu$ is the number of degrees of freedom, and $\delta\phi$ and $\delta m$ are the uncertainties in the measured phase and modulation values, respectively. $\delta\phi = 0.2°$ and $\delta m = 0.005$ are preferred.

Thus, in accordance with the present invention, there is provided an inexpensive semiconductor laser diode having a modulated electrical input and producing a large number of photons which excite a fluorescent material to emit fluorescence radiation which can be measured as an indication of fluorescence lifetime (or decay). The measurements can be made using a phase-modulation or a frequency-domain technique. The present invention allows fluorescence measurements up to an upper modulation frequency of about 3.8 GHz, and allows the resolution of mixtures of fluorophores exhibiting different lifetimes.

Other objects, features and advantages of the present invention will become apparent to those skilled in the art from the above detailed description and following Examples of the present invention. It should be understood, however, that the description and specific examples, while indicating preferred embodiments of the present invention, are given by way of illustration and not limitation. Many changes and modifications within the scope of the present invention may be made without departing from the spirit thereof, and the present invention includes all such modifications.

EXAMPLE 1

Apparatus for Fluorescence Measurement Using a Semiconductor Laser Diode as a Light Source An example of a laser-diode frequency-domain fluorometer according to the present invention is shown in FIG. 1. A laser diode 3, such as a 410 nm light pulser Model PLP-01 produced by Hamamatsu or equivalent thereof and consisting of a LDH-041-CS laser diode head with a C3551-02 controller, emits a series of output light pulses with a maximum repetition frequency of 10 MHz, a constant peak power of 0.44 mW, and a pulse duration of 40 ps. The pulsed light source has an average power of 220 nW at the 10 MHz repetition rate. Thus, the laser light source operates as an intensity-modulated light source at the pulse repetition frequency, and has all the harmonics of that frequency. Owing to the short pulse duration of 40 ps, efficient intensity-modulation is available up to 11 GHz. A fluorescence sample 4 is positioned close to the LDH-041-CS laser diode head in order to capture as much excitation light as possible. The diode laser 3 is triggered by the first frequency synthesizer 5a, and generates an electrical trigger output for the third frequency synthesizer 5c. The second frequency synthesizer 5b can be used to coherently drive the LO inputs of mixers 7 and 9 at a slightly different frequency. The Gigatronics model 905 frequency synthesizer 5b thus is phaselocked to the diode laser, and generates the RF signal for the reference mixer 7.

The diode laser is directed towards the sample compartment to generate sample fluorescence. A Hamamatsu model R2566UMCP microchannel plate (MCP) photo-multiplier (PMT) 6 is used to measure scattered radiation from the diode laser 3, as well as to measure fluorescence light from the sample 4. The PMT 6 is an externally cross-correlated micro-channel plate PMT. The technique of cross-correlation is well known for its use in phase-modulation or frequency-domain fluorometers as a means to increase the signal-to-noise ratio and to reject unwanted harmonics. The output signal from the PMT 6 is down-mixed to 25 Hz in the signal mixer 9, and input to the SLM instruments phase meter 8. The phase meter 8 also receives an input signal from reference mixer 7 for comparison with the input signal from signal mixer 9. A direct current (DC) signal channel (not shown) also connects PMT 6 with the phase meter 8. The AC signal and the DC signal are processed within the phase meter 8 to obtain the modulation information, which is the ratio of the AC/DC components of the modulation emission.

In order to be useful for frequency-domain fluorometry, the pulsed laser diode should provide harmonic content over a wide range of modulation frequencies. Due to the frequency-dependent response of the detector and associated electronics, it is difficult to know in advance, in absolute terms, the extent of modulation at each frequency. To circumvent this difficulty, the modulation and phase of the sample fluorescence light, relative to that of scattered light from the laser diode 3, is measured. Owing to this procedure, the apparatus response is eliminated.

Figure 2:
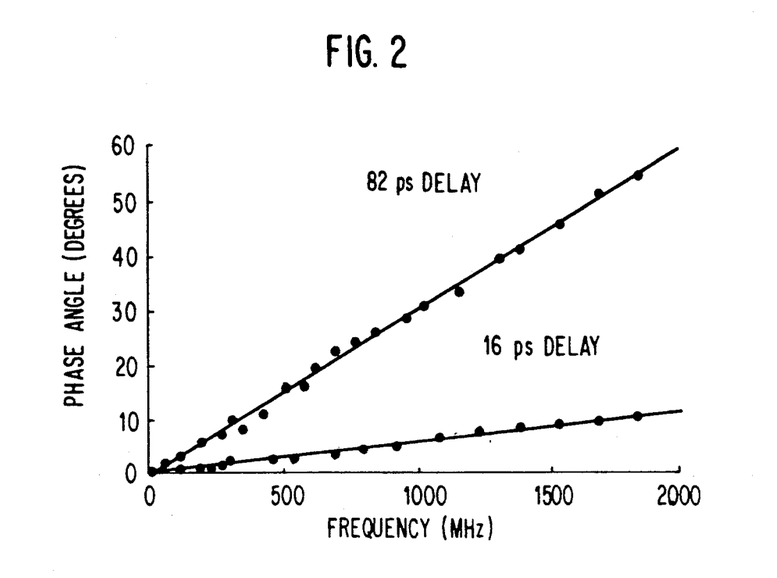
FIG. 2 is a graph showing the phase accuracy of the laser diode fluorometer measured using known optical delays of 16 and 82 ps.

Optical delays to simulate very short fluorescence lifetimes were used in the testing of the above-described configuration. In these tests, the signal phase, including the optical delay, was measured relative to the reference signal phase. In a second step, the signal phase without the optical delay was measured again. The phase differences between the phase readings of step 1 and step 2 are shown in FIG. 2. This procedure corresponds completely to the procedure used in fluorescence lifetime measurements. As expected, the modulation of the delayed light relative to that of the undelayed light did not change with frequency, and was very close to 100%. In FIG. 2, the measured phase shift versus modulation frequency is shown for optical delays of 16 and 82 ps. As expected, the delay-generated phase shifts versus frequency show a linear relationship, and the measured values (points in FIG. 2) agree with the theoretical values (lines in FIG. 2).

The configuration in accordance with the present invention was found to be suitable for use with fluorophores with lifetimes ranging from 0.5 to 6.4 ns, which were known to be standard for single-exponential decays. These fluorophores were chromatographically pure and placed in spectroscopic grade toluene and dimethylformamide solvents. The solutions were purged by nitrogen before the measurements. The emission was observed through a Corning 3-73 band-pass filter which absorbs the emission and/or scattered light below 420 nm. Frequency responses for perylene in toluene and 4-dimethylamino-4'methoxystilbene (DMS) in dimethylformamide are shown in FIG. 3.

The experimental data (FIG. 3) are well fit by the solid lines representing the best single-exponential fits, and the deviations (lower panel) are random. For perylene the value of $\chi^2_R = 1.2$ indicates no significant elevation in the extent of random noise in the data. For DMS $\chi^2_R = 10.9$, which indicates an approximate threefold increase in $\delta\phi$ to 0.6° and $\delta m$ to 0.015. The fit could not be improved by use of the double-exponential model

[Eq. (1) with i=2], which indicates that the elevated value of $\chi^2_R$ is due to random noise and not systematic errors and/or a multi-exponential decay for DMS.

Figure 4:
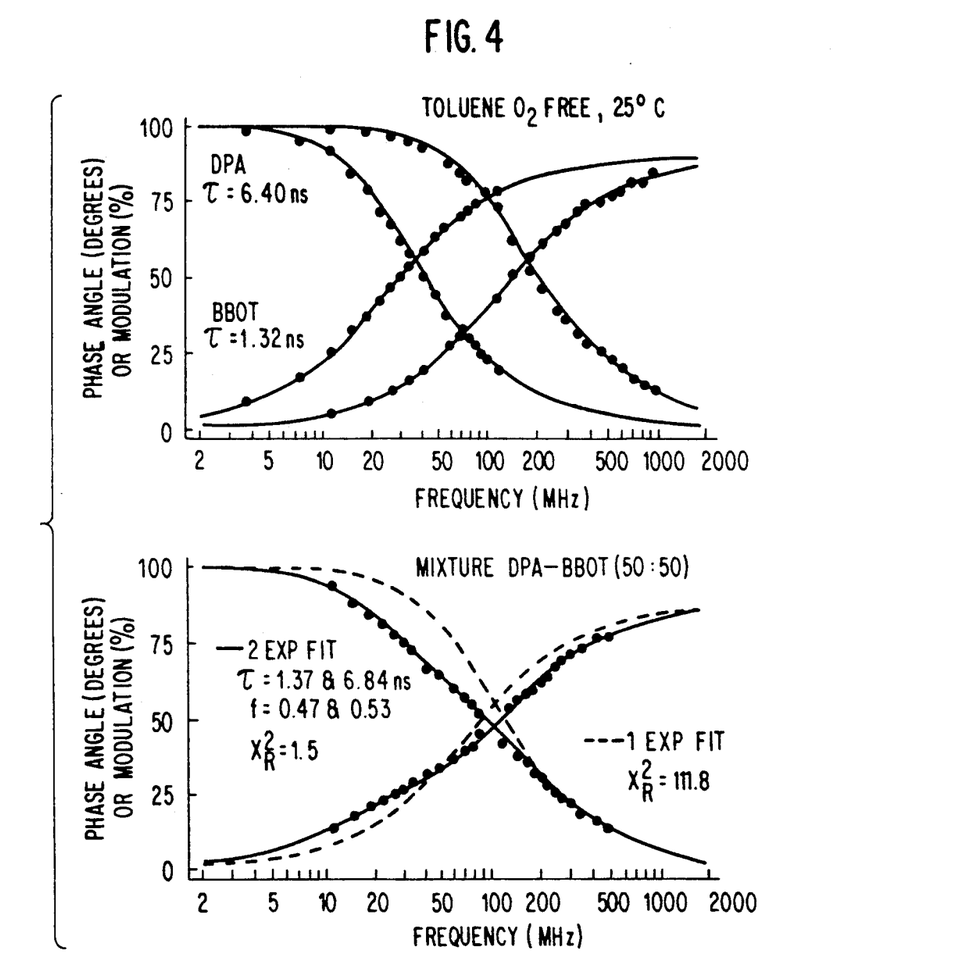

The PLP-01 was also tested for use in the resolution of a multi-exponential decay. For this purpose, two fluorophores, diphenylanthracene (DPA), and 2,5-bis [5-tert-butylbenzoxazolyl (2)] thiophene (BBOT), each which shows single-exponential decay times of 6.40 and 1.32 ns, respectively (FIG. 4, top) were chosen. Frequency-domain data for the 91:1 mixture are shown in FIG. 4, bottom, which shows the frequency response for a mixture of DPA (6.40 ns) and BBOT (1.32 ns). The presence of multiple decay times is immediately evident from an attempt to fit the data to a single decay time. The best single decay time fit, shown as the dashed line, is obviously inadequate. In contrast, the data can be explained by a curve with decay times of 6.84 and 1.37 ns and near equal amplitudes (solid line). The expected amplitudes are $f_1=0.5$ and $f_2=0.5$, where $f_1=\alpha_i\tau_i/\Sigma\alpha_i\tau_i$.

Thus, in accordance with the present invention, there is provided an inexpensive semiconductor laser diode having a modulated electrical input and producing a large number of photons which excite a fluorescent material to emit fluorescence radiation which can be measured as an indication of fluorescence lifetime (or decay). The measurements can be made by using a phase-modulation and/or frequency-domain technique. The present invention allows the resolution of mixtures of fluorophores exhibiting different lifetimes.

An additional advantage of using laser diodes in fluorometry is the resulting decreased autofluorescence at long excitation and emission wavelengths. To date, few such measurements of long wavelength reduced fluorescence have been performed because only a limited number of fluorophores have been identified. Nonetheless, it is probable that many additional fluorophores will be identified in the future for specific sensing purposes, and the laser diodes will be ideal excitation sources for these probes.

Preferred embodiments of the invention are described above, but it is to be understood that various changes and modifications may be made without departing from the spirit of the invention whose scope is defined by the following claims.

What is claimed is:

1. An apparatus for detecting, in the frequency-domain, a change in phase angle and/or modulation, corresponding to a change in a lifetime in a range from about 50 ps to 100 ns, of a fluorescence emission of at least one fluorophore comprising:
   semiconductor laser diode means which outputs modulated light when driven by a first electrical signal, said light being substantially monochromatic and coherent;
   first electrical signal generator means (5a), coupled to said semiconductor laser diode means, for generating said first electrical signal to cause said semiconductor laser diode means to output said modulated light having a wavelength which excites said at least one fluorophore to emit fluorescence; and
   second electrical signal generator means (5b), having a synchronization port coupled to said first electrical signal generator means or to an auxiliary electrical signal corresponding to the light output of said laser diode means, said second electrical signal generator means generating at a signal output port thereof a second electrical signal that is phase locked to a modulation phase of said light output of said laser diode means;
   a first electrical signal mixer (7) and a second electrical signal mixer (9), said first mixer being responsive to said second electrical signal and to a signal derived from said first electrical signal to produce a first difference-frequency signal;
   photodetector means for sensing said emitted fluorescence, said photodetector means being coupled via said second mixer to said second electrical signal generator means to produce a second difference-frequency signal representative of a change in phase angle and/or modulation of said emitted fluorescence of said at least one fluorophore, wherein said change corresponds to a change in fluorescence lifetime; and
   comparator means for comparing the second difference-frequency signal with the first difference-frequency signal to produce a signal indicative of said change in fluorescence.

2. The apparatus of claim 1, wherein (a) said laser diode means further comprises a photodiode that generates said auxiliary electrical signal corresponding to the output of said laser diode.

3. The apparatus of claim 1, wherein said laser diode means outputs said modulated light with a plurality of frequency components that are harmonics of said first electrical signal.

4. The apparatus of claim 1, wherein said wavelength of said modulated light is in a range of 250–1600 nm and said wavelength is selected from
   (i) a fundamental wavelength of said output modulated light of said laser diode means; and
   (ii) a resultant wavelength, after frequency doubling, of a fundamental wavelength of said output modulated light of said laser diode means.

5. The apparatus of claim 2, wherein said laser diode means is intrinsically or extrinsically modulated in the frequency range of 10 kHz to 20 GHz to produce said modulated light in the form of light pulses having a pulse duration in a range of 5 to 50 ps.

6. The apparatus of claim 1 wherein said photodetector means further comprises:
   means for measuring relative modulation of said first and said second difference-frequency signals as an indication of said change in phase angle and/or modulation of said emitted fluorescence of said at least one fluorophore.

7. The apparatus according to claim 1, wherein said photodetector means comprises a photomultiplier tube for sensing said emitted fluorescence.

8. A method for detecting, in the frequency-domain, changes in phase angle and/or modulation, corresponding to changes in a lifetime in a range of 50 ps to 100 ns, of emitted fluorescence of at least one fluorophore in a sample, comprising the steps of:
   driving a semiconductor laser diode means with a first electrical signal to cause said semiconductor laser diode means to output modulated light having a wavelength capable of exciting said at least one fluorophore to emit fluorescence, wherein said modulated light is monochromatic and coherent;
   exciting said at least one fluorophore with said modulated light to produce a fluorescence emission;
   generating a second electrical signal, coupled to said first electrical signal or to an auxiliary electrical signal corresponding to the light output of said laser diode means, said second electrical signal being phase locked to said light output of said laser diode means;

sensing said fluorescence emission to provide a third electrical signal corresponding to said fluorescence emission; and comparing said second electrical signal with said third electrical signal to generate a difference signal representative of said change in phase angle and/or modulation, corresponding to a change in lifetime, of said emitted fluorescence of said at least one fluorophore.

9. The method of claim 8 wherein said laser diode outputs modulated light with a plurality of frequency components that are harmonics of said electrical signal.

10. The method of claim 8, wherein said wavelength is in the range of 250-1600 nm, and said wavelength is selected from (i) a fundamental wavelength of said output of said laser diode means; and (ii) a resultant wavelength, after frequency doubling, of a fundamental wavelength of said output of said laser diode means.

11. The method of claim 8, wherein said comparing step comprises measuring a phase difference between said corresponding third electrical signal of said emitted fluorescence and the second electrical signal.

12. The method of claim 8, wherein said change corresponds to the presence or concentration an analyte in a sample, wherein said sample is a compound, a mixture, a surface, a solution, an emulsion, a suspension, a mixture, a cell culture, a fermentation culture, a cell, a tissue, a secretion or a derivative or extract thereof.

13. A method according to claim 8, wherein said analyte comprises a salt, a derivative, a polymer, a dissociation product, or aggregate of said analyte.

14. A method according claim 12, wherein said analyte is selected from $H^+$, $OH^-$, $O_2$, $CO_2$, $H_2CO_3$, $HCO_3$, $Ca^{++}$, or $K^+$.

15. A method according to claim 8, wherein said modulated light is intrinsically modulated or extrinsically modulated.

16. The method o claim 8, wherein said driving step comprises driving the semiconductor laser diode means with said first electrical signal having a frequency in the range of 10 kHz to 20 GHz to produce said modulated light in the form of light pulses having a pulse duration in a range of 5 to 50 ps.

* * * * *